US006949175B2

(12) United States Patent
Sugiyama et al.

(10) Patent No.: US 6,949,175 B2
(45) Date of Patent: Sep. 27, 2005

(54) GAS SENSING ELEMENT

(75) Inventors: Tomio Sugiyama, Nagoya (JP);
Takehito Kimata, Ichinomiya (JP)

(73) Assignee: Denso Corporation, (JP)

( * ) Notice: Subject to any disclaimer, the term of this patent is extended or adjusted under 35 U.S.C. 154(b) by 0 days.

(21) Appl. No.: 10/001,800

(22) Filed: Dec. 5, 2001

(65) Prior Publication Data
US 2002/0070111 A1 Jun. 13, 2002

(30) Foreign Application Priority Data

Dec. 7, 2000 (JP) ............................. 2000-373363
Oct. 15, 2001 (JP) ............................. 2001-317049

(51) Int. Cl.[7] ............................................ G01N 27/41
(52) U.S. Cl. ...................... 204/429; 204/427; 73/23.32
(58) Field of Search .............................. 204/425, 426, 204/427, 428, 429; 73/23.31, 23.32; 205/784.5

(56) References Cited

U.S. PATENT DOCUMENTS

| | | | |
|---|---|---|---|
| 4,718,999 A | * 1/1988 | Suzuki et al. ............... | 204/406 |
| 4,798,693 A | 1/1989 | Mase et al. | |
| 5,160,598 A | 11/1992 | Sawada et al. | |
| 5,169,513 A | * 12/1992 | Mase et al. .................. | 204/429 |
| 5,302,276 A | * 4/1994 | Kato et al. ................... | 204/429 |
| 5,326,597 A | 7/1994 | Sawada et al. | |
| 5,419,828 A | * 5/1995 | Nakano et al. ............. | 204/425 |
| 5,522,979 A | 6/1996 | Tatumoto et al. | |
| 5,733,504 A | 3/1998 | Paulus et al. | |
| 5,766,434 A | * 6/1998 | Fujii et al. .................. | 204/429 |
| 5,925,814 A | 7/1999 | Tsuzuki et al. | |
| 6,210,641 B1 | 4/2001 | Yamada et al. | |

FOREIGN PATENT DOCUMENTS

| | | |
|---|---|---|
| DE | 4408504 | 9/1995 |
| DE | 19938416 | 3/2000 |
| JP | 60-228955 | 11/1985 |
| JP | 02-212758 | 8/1990 |
| JP | 07-260741 | 10/1995 |
| JP | 8-5603 | 1/1996 |
| JP | 09 068515 | 3/1997 |
| JP | 10-221287 | 8/1998 |
| JP | 11-237361 | 8/1999 |
| WO | WO 0005573 | 2/2000 |

OTHER PUBLICATIONS

Logothetis et al, High-Temperature Oxygen Sensors Based on Electrochemical Oxygen Pumping, ACS Symposium Series 309 pp. 136-154, 1986.*

Moriyama et al; "Development of a Fast-Response Air-Fuel Ration Meter Utilizing the Extended Range Oxygen Sensor"; Nissan Technical Report No. 22; pp. 94-101, Dec. 1986.

Takeuchi; "Porous Materials; Characterization, Production and Application"; Meiji University; pp. 335-337; no date.

* cited by examiner

Primary Examiner—Kaj K. Olsen
(74) Attorney, Agent, or Firm—Nixon & Vanderhye PC

(57) ABSTRACT

A gas sensing element includes a solid electrolytic substrate having oxygen ion conductivity, a measured gas side electrode provided on a surface of the solid electrolytic substrate so as to be exposed to a measured gas, and a reference gas side electrode provided on another surface of the solid electrolytic substrate so as to be exposed to a reference gas. The measured gas side electrode is covered by a porous electrode protecting layer. A limit current density of the electrode protecting layer is in a range from 0.04 mA/mm$^2$ to 0.15 mA/mm$^2$ on a unit area of the reference gas side electrode.

11 Claims, 6 Drawing Sheets

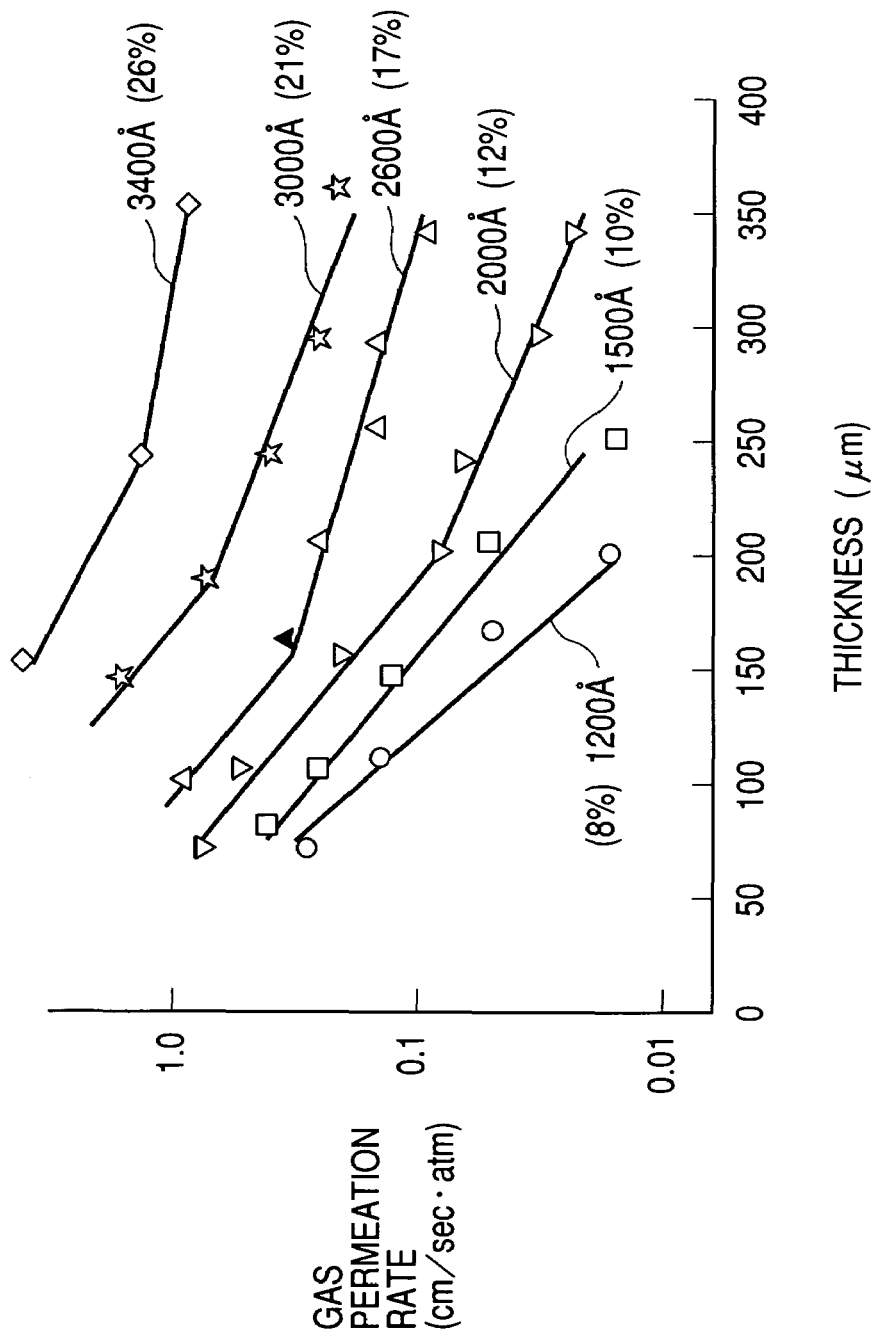

GAS SENSING ELEMENT

BACKGROUND OF THE INVENTION

This invention relates to a gas sensing element utilized for controlling the combustion of an internal combustion engine for an automotive vehicle or the like.

To control the combustion of an automotive engine, a gas sensor is installed in an exhaust system of an automotive engine. The gas sensor comprises a gas sensing element arranged in the following manner.

The gas sensing element comprises a solid electrolytic substrate having oxygen ion conductivity, a measured gas side electrode provided on a surface of this solid electrolytic substrate so as to be exposed to a measured gas, and a reference gas side electrode provided on another surface of the solid electrolytic substrate so as to be exposed to a reference gas.

Furthermore, the measured gas side electrode is covered by a porous protecting layer. The reference gas side electrode is provided in a reference gas chamber storing the reference gas. A heater, integrally formed with the solid electrolytic substrate, promptly increases the temperature of the gas sensing element to a predetermined activation level capable of detecting a gas concentration.

The role of the electrode protecting layer is to protect the electrode from heat of a measured gas and contamination by poisonous substances.

Furthermore, the electrode protecting layer has a role of promoting the diffusion of a measured gas to advance the reaction of HC and CO contained in the measured gas on a measured gas side electrode with O2 supplied from a reference gas side electrode.

However, providing the electrode protecting layer solely for the purpose of protecting the electrode from poisonous substances will increase the flow resistance of the measured gas flowing therethrough and accordingly worsen the response of a gas sensing element.

On the other hand, providing the electrode protecting layer solely for the purpose of improving the response will fail in preventing the poisonous substances from passing through the electrode protecting layer and accordingly deteriorate the output of a gas sensing element due to contamination of the electrode. Thus, the endurance of the gas sensing element will worsen.

Unexamined Japanese patent publications Nos. 60-228955 and 8-5603 disclose conventional manufacturing methods relating to an electrode protecting layers provided on a measured gas side electrode.

The former patent application discloses a method for manufacturing a gas sensing element having porous layers provided on the surfaces of a sensing portion and a heater portion of the gas sensing element, thereby preventing the gas sensing element from bowing during a sintering operation.

The latter patent application discloses a method for manufacturing a gas sensing element having a porous electrode protecting layer provided on a solid electrolytic substrate with a contraction rate of the electrode protecting layer being equalized with that of the solid electrolytic substance, thereby preventing the gas sensing element from bowing during a sintering operation. To this end, the material for the electrode protecting layer and a surface to volume ratio of the electrode protecting layer are regulated. However, it is difficult for these conventional manufacturing methods to surely satisfy both of the response and endurance requirements. Accordingly, it is earnestly required to provide an excellent gas sensor capable of satisfying such requirements.

Furthermore, unexamined Japanese patent publication No. 10-221287 discloses a gas sensing element comprising a structural member having gas permeation holes. However, even for this prior art, it is difficult to surely satisfy both of the response and endurance requirements.

SUMMARY OF THE INVENTION

To solve the above-described problems, the present invention has an object to provide a gas sensing element having excellent response and anti-poisoning endurance.

In order to accomplish the above and other related objects, the present invention provides a gas sensing element comprising a solid electrolytic substrate having oxygen ion conductivity, a measured gas side electrode provided on another surface of the solid electrolytic substrate so as to be exposed to a measured gas, and a reference gas side electrode provided on a surface of the solid electrolytic substrate so as to be exposed to a reference gas, wherein the measured gas side electrode is covered by a porous electrode protecting layer, and a limit current density of the electrode protecting layer is in a range from 0.04 $mA/mm^2$ to 0.15 $mA/mm^2$ on a unit area of the reference gas side electrode under the following conditions:

an oxygen concentration in the measured gas is 0.1%, a measurement temperature and an element temperature (an element surface temperature at the measured gas side of a sensing portion) are not less than 600° C., and a voltage applied between the measured gas side electrode and the reference gas side electrode is 0.5 V (i.e., an oxygen pumping in the direction from the measured gas side to the reference gas side).

The gas sensing element of the present invention is characterized in that the measured gas side electrode is covered by the electrode protecting layer whose limit current density is in the range from 0.04 $mA/mm^2$ to 0.15 $mA/mm^2$ under the above-described conditions.

When the limit current density is less than 0.04 $mA/mm^2$, the porous electrode protecting layer may be clogged or blocked by poisonous substances contained in the measured gas. The measured gas cannot pass through the electrode protecting layer. The response of the gas sensing element will worsen at an earlier stage of the expected life of this gas sensing element.

When the limit current density is larger than 0.15 $mA/mm^2$, the poisonous substances contained in the measured gas can easily pass through the electrode protecting layer and therefore the electrode will be considerably clogged or blocked by the poisonous substances. The sensor output may not be produced.

The above-described sensing portion is a portion substantially relating to the gas concentration measurement of the gas sensing element and is in the vicinity of the measured gas side electrode and the reference gas side electrode.

The gas sensing element of the present invention has the following functions and brings the following effects.

The gas sensing element of the present invention detects an oxygen concentration in a measured gas based on an oxygen ion current flowing between a reference gas side electrode and a measured gas side electrode.

According to the present invention, the electrode protecting layer is provided on the measured gas side electrode in such a manner that the limit current density of the oxygen ion current is in the above-described range under the above-described conditions. Thus, it becomes possible to obtain a gas sensing element capable of preventing the protecting layer from being clogged or blocked by the poisonous substances contained in the measured gas and accordingly having excellent endurance.

Furthermore, the measured gas can smoothly flow across the electrode protecting layer. Thus, even when the oxygen concentration in a measured gas changes rapidly, the gas sensing element can produce a sensor output varying quickly according to a change of the oxygen concentration (refer to later-explained FIGS. 5 and 6).

The gas sensing element of the present invention is an element capable of measuring an oxygen concentration in a measured gas based on an electromotive force.

As apparent from the foregoing, the present invention provides a gas sensing element having excellent response and anti-poisoning endurance.

BRIEF DESCRIPTION OF THE DRAWINGS

The above and other objects, features and advantages of the present invention will become more apparent from the following detailed description which is to be read in conjunction with the accompanying drawings, in which:

FIG. 8 is a graph showing a relationship between a gas permeation rate, a thickness, and an average pore diameter (i.e., porosity) of the electrode protecting layer in accordance with the preferred embodiment of the present invention.

DESCRIPTION OF THE PREFERRED EMBODIMENT

Figure 1:
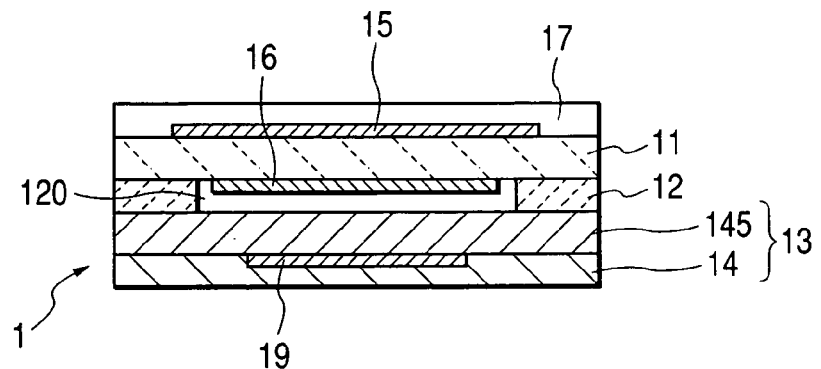
FIG. 1 is a cross-sectional view showing a gas sensing element in accordance with a preferred embodiment of the present invention.

A preferred embodiment of the present invention will be explained hereinafter with reference to attached drawings. Identical parts are denoted by the same reference numerals throughout the drawings.

A gas sensing element in accordance with a preferred embodiment of the present invention will be explained hereinafter with reference to FIGS. 1 to 8.

As shown in FIG. 1, the gas sensing element 1 of the preferred embodiment of the present invention comprises a solid electrolytic substrate 11 having oxygen ion conductivity, a measured gas side electrode 15 provided on one surface of the solid electrolytic substrate 11 so as to be exposed to a measured gas, and a reference gas side electrode 16 provided on another surface of the solid electrolytic substrate 11 so as to be exposed to a reference gas. The measured gas side electrode 15 is covered by a porous electrode protecting layer 17. A limit current density of the electrode protecting layer 17 is in a range from 0.04 $mA/mm^2$ to 0.15 $mA/mm^2$ on a unit area of the reference gas side electrode under the following conditions.

An oxygen concentration in the measured gas is 0.1%. A measurement temperature and an element temperature (an element surface temperature at the measured gas side of a sensing portion) are not less than 600° C., and a voltage applied between the measured gas side electrode 15 and the reference gas side electrode 16 is 0.5 V (i.e., an oxygen pumping in the direction from the measured gas side to the reference gas side).

To control the combustion of an automotive engine, the gas sensing element 1 of this embodiment is installed in an exhaust gas system and detects an oxygen concentration in the exhaust gas.

Figure 2:
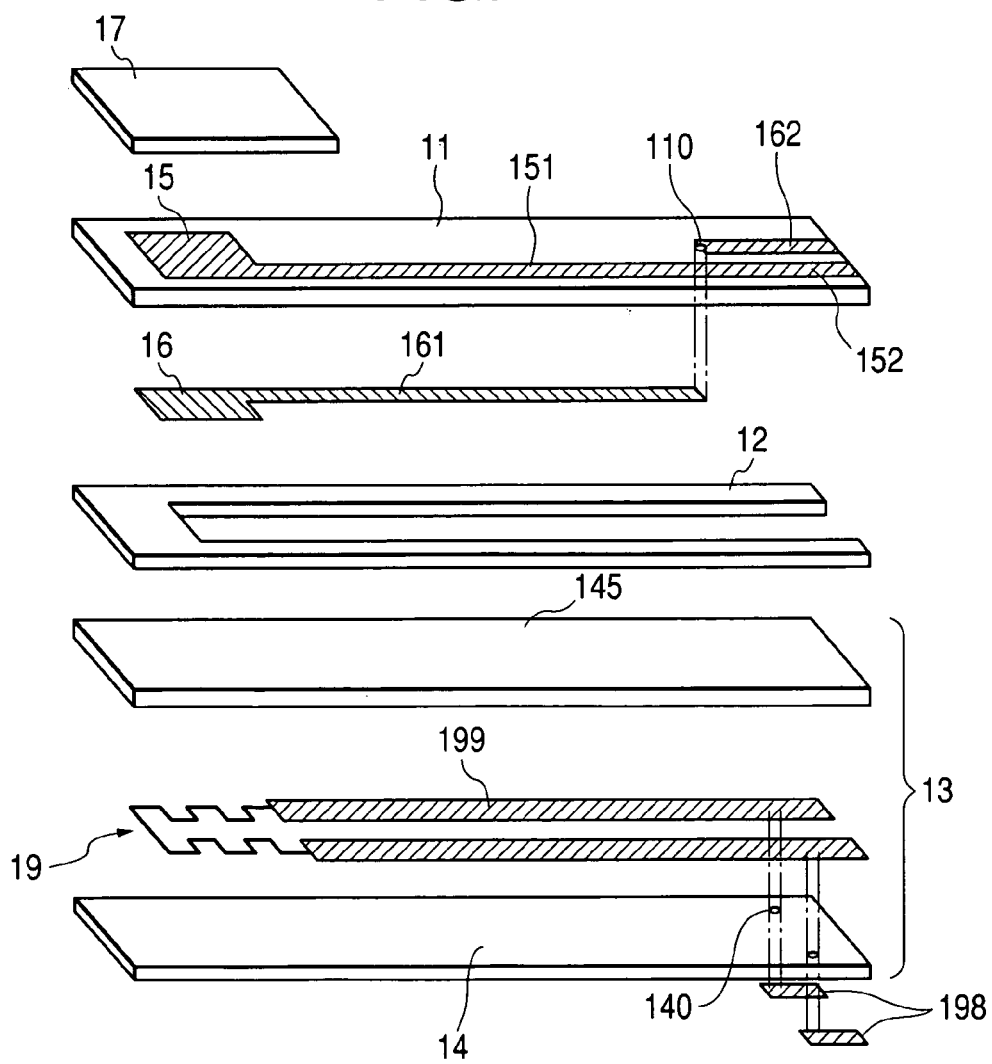
FIG. 2 is a perspective exploded view showing the gas sensing element in accordance with the preferred embodiment of the present invention.

Hereinafter, the gas sensing element 1 of this embodiment will be explained in greater detail. As shown in FIGS. 1 and 2, the gas sensing element 1 comprises a spacer 12 laminated next to the solid electrolytic substrate 11 for defining a reference gas chamber 120, and a heater 13 laminated next to the spacer 12.

The heater 13 comprises an insulating substrate 145 and a heater substrate 14. A heater element 19 is provided on the surface of heater substrate 14. Electric power is supplied to the heater element 19 via leads 199 provided on one surface of the heater substrate 14 and terminals 198 provided on an opposite surface of the heater substrate 14. Through holes 140 are opened across the heater substrate 14 to electrically connect the leads 199 to corresponding terminals 198.

The measured gas side electrode 15 is provided on one surface of the solid electrolytic substrate 11 and is covered by the electrode protecting layer 17.

The reference gas side electrode 16 is provided on the opposite surface of the solid electrolytic substrate 11 so as to face the reference gas chamber 120.

A lead 151 and its terminal 152, provided on the same surface of the solid electrolytic substrate 11, are electrically connected to the measured gas side electrode 15. A lead 161 and its terminal 162, provided on the opposite surfaces of the solid electrolytic substrate 11 and electrically connected via a through hole 110, are electrically connected to the reference gas side electrode 16.

The spacer 12 has a U-shaped configuration to define the reference gas chamber 120 between the insulating substrate 145 and the solid electrolytic substrate 11.

Next, a method for manufacturing the gas sensing element 1 will be explained.

First, a green sheet for the solid electrolytic substrate 11 is fabricated in the following manner.

The prepared material are zirconia and yttria whose grain sizes are regulated in a predetermined level. First 94.0 mol % zirconia and 6.0 mol % yttria are disposed to obtain a mixed powder. Then, the mixed powder (100 weight part) is added with $SiO^2$ (0.15 weight part) and $Al_2O_3$ (2.0 weight), and ground and mixed together in a pot mill for a predetermined time. Next, the obtained ground mixture is mixed with an organic solvent (e.g., mixed solution of ethanol and toluene), a binder (polyvinyl butyral), and a plasticizing agent (di-butyl phthalate) to obtain a slurry.

Next, the obtained slurry is processed according to the doctor blade method to configure it into a unburnt zirconia sheet having a thickness of 0.2 mm. The obtained zirconia sheet is cut into a rectangular shape of 5 mm×70 mm. The through hole 110 is opened at a predetermined portion of the sheet to electrically connect the lead 161 and its terminal 162.

Then, a Pt paste containing zirconia is applied on the surface of the sheet by screen printing to form the print portions of measured gas side electrode 15, reference gas side electrode 16, leads 151 and 161, and terminals 152 and 162. Through the above fabrication processes, the green sheet for the solid electrolytic substrate 11 is obtained.

An alumina green sheet for the spacer 12, the insulating substrate 145, and the heater substrate 14 is fabricated in the following manner.

By using a pot mill, an alumina powder having a predetermined grain size is mixed with an organic solvent (mixed solution of ethanol and toluene), a binder (polyvinyl butyral), and a plasticizing agent (di-butyl phthalate) for a predetermined time to obtain a slurry.

Next, the obtained slurry is processed according to the doctor blade method to configure it into a unburnt alumina sheet having a thickness of 0.4 mm.

The obtained alumina sheet is cut into a total of three rectangular sheets each having a size of 5 mm×70 mm.

Two of the three rectangular sheets are directly used for the heater substrate 14 and the insulating substrate 145. The remaining one rectangular sheet is further cut to have a cutout of 2 mm×67 mm for the spacer 12.

Furthermore, two through holes 140 are opened at end portions on the sheet for the heater substrate 14 to electrically connect the leads 199 and their terminals 198. Then, a Pt paste containing alumina is applied on the surface of the sheet of heater substrate 14 by screen printing to form the print portions of the heater element 19, the leads 199, and terminals 198.

A green sheet for the electrode protecting layer 17 is fabricated in the following manner.

By using a pot mill, an alumina powder having a predetermined grain size (larger than that of the material used for the heater substrate 14) is mixed with an organic solvent (mixed solution of ethanol and toluene), a binder (polyvinyl butyral), and a plasticizing agent (di-butyl phthalate) for a predetermined time to obtain a slurry.

Next, the obtained slurry is processed according to the doctor blade method to configure it into a sheet. The obtained sheet is cut into a unburnt alumina sheet having a thickness of 0.2 mm. The obtained sheet is cut into a rectangular shape of 5 mm×30 mm to obtaine the green sheet for the electrode protecting layer 17.

The zirconia green sheet and the alumina green sheets thus fabricated are stacked in a predetermined order (as shown in FIG. 2) and pressed together to obtain a lamination body. The pressed lamination body is then sintered at 1,500° C. for one hour, thereby obtaining the gas sensing element 1 shown in FIGS. 1 and 2.

The gas sensing element 1 detects an oxygen concentration in a measured gas according to the following principle.

Figure 3:
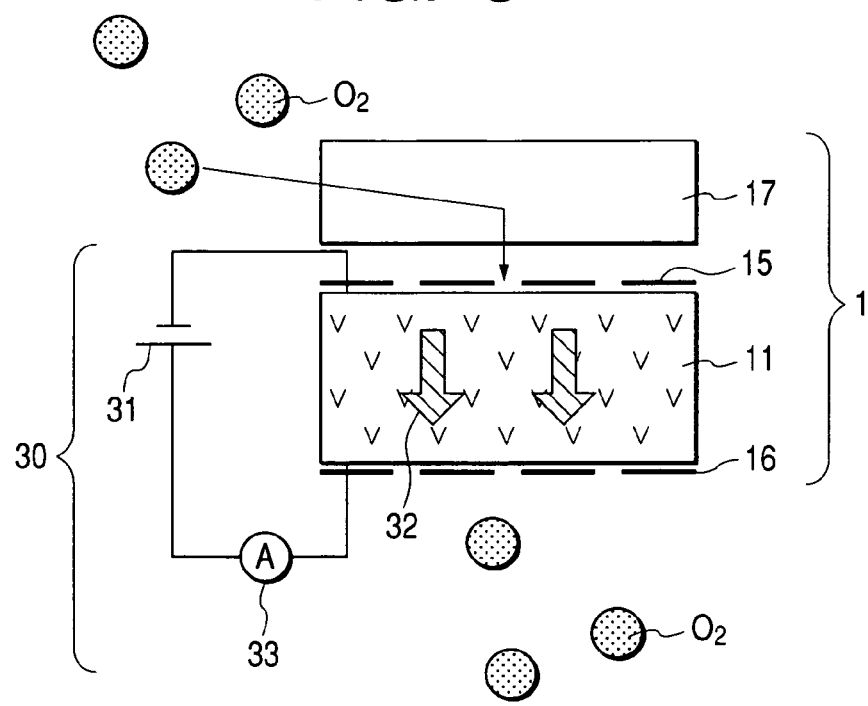
FIG. 3 is a view explaining the measurement principle of the gas sensing element in accordance with the preferred embodiment of the present invention.

FIG. 3 is a view showing a model of gas sensing element 1.

The measured gas side electrode 15 and the reference gas side electrode 16 are provided on opposite surfaces of the solid electrolytic substrate 11. A predetermined voltage of an external power source 31 is applied between these electrodes 15 and 16.

According to this arrangement, oxygen molecules contained in the measured gas reach the measured gas side electrode 15 via the electrode protecting layer 17 and turns into oxygen ions 32.

The oxygen ions 32 reach the reference gas side electrode 16 via the solid electrolytic substrate 11 and then return the oxygen molecules again.

An ammeter 33, provided in a power supply circuit 30 of the power source 31, measures an oxygen ion current flowing between the electrodes 15 and 16 across the solid electrolytic substrate 11.

Figure 4:
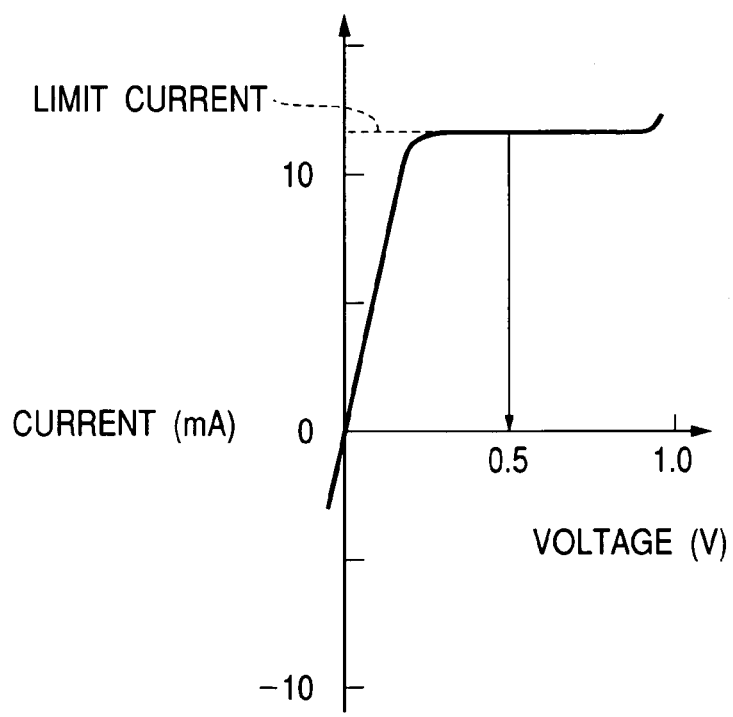
FIG. 4 is a graph showing a relationship between an applied voltage and a resulting current together with a limit current.

FIG. 4 shows the behavior of a sensor current responsive to a voltage applied between the electrodes 15 and 16 of the gas sensing element 1.

According to the characteristics shown in FIG. 4, there is a flat region where the current does not vary with increasing voltage. The current value in this flat region is generally referred to as a limit current. Furthermore, a limit current value per a unit electrode area is introduced as a limit current density. The limit current density is obtained by dividing the current flowing in the power supply circuit 30 by an area of the reference gas side electrode.

According to the disclosed embodiment, the applied voltage is 0.5 V and therefore the limit current flowing between the electrodes 15 and 16 is equal to the limit current.

The limit current varies in proportion to an oxygen concentration. It is usual in an ordinary engine exhaust system that the current flowing between the electrodes 15 and 16 is equal to the limit current when the applied voltage is 0.5V.

Figure 5:
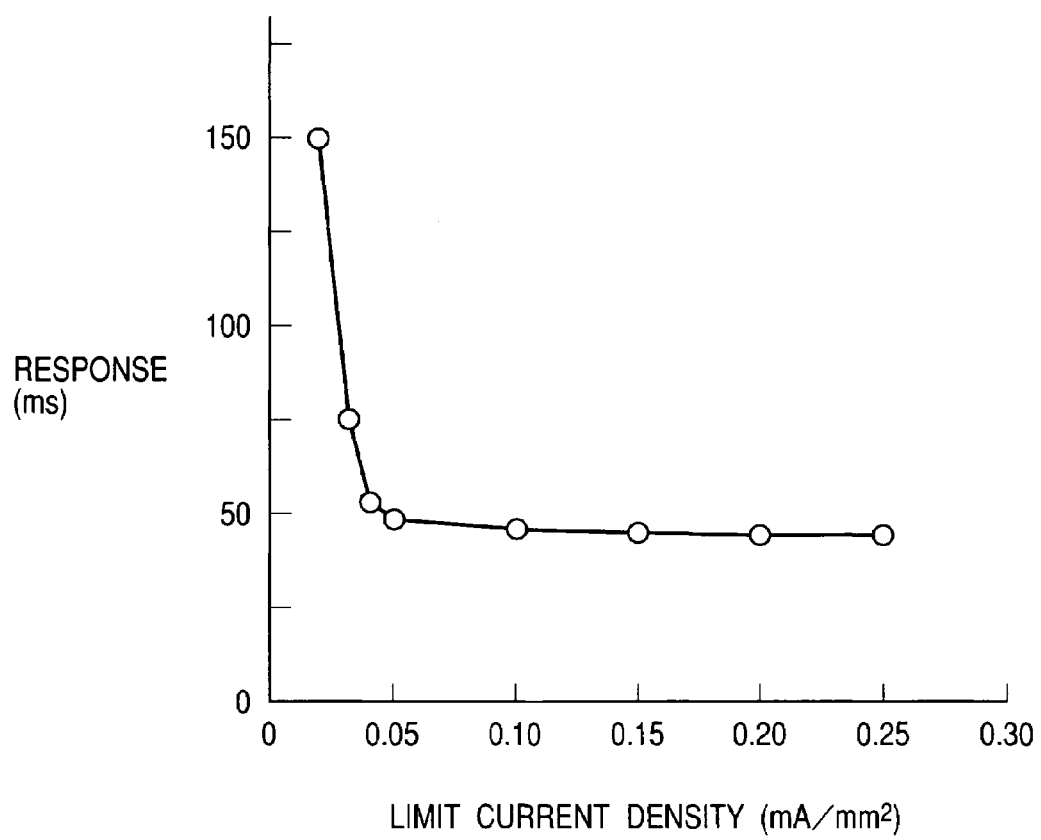
FIG. 5 is a graph showing a relationship between a limit current density and response in accordance with the preferred embodiment of the present invention.

The performance of the gas sensing element 1 was evaluated on numerous gas sensing elements manufactured according to the above-described manufacturing method. As a measurement result, FIG. 5 shows a relationship between the limit current density and the sensor response.

The following is a measurement method.

First, each tested gas sensing element is incorporated into an assembly in the same manner as an ordinary automotive exhaust gas sensor. Each assembly is used as an evaluation sample.

Each evaluation sample was exposed to a measured gas (having an oxygen concentration of 0.1% and a gas temperature of 600° C.). The temperature of the gas sensing element (i.e., an element surface temperature at the measured gas side of a sensing portion) was set to 650° C. The performance evaluation was performed according to the above-described detecting principle.

The voltage applied between two electrodes was increased up to 1 V at a rate of 1V/100 sec. A limit current value corresponding to 0.5 V was obtained and divided by the area of the reference gas side electrode to obtain the limit current density.

Regarding the response, the tested evaluation sample was installed in an exhaust pipe of a practical automotive engine to evaluate a response time require to reach a 63% level in the voltage change from rich to lean at the exhaust gas temperature of 400° C. and the element temperature of 550° C.

According to FIG. 5, the sensor response is bad in the region where the limit current density is less than 0.04 mA/mm². On the other and, the response is good in the region where the limit current density is equal to or larger than 0.04 mA/mm².

Next, an endurance test of the evaluation sample was performed by exposing the evaluation sample in an exhaust gas for 100 hours at the exhaust gas temperature of 600° C. and the element temperature of 650° C. according to an endurance bench test using a practical engine. In this endurance test, an oil component was added to engine fuel by an amount 0.7 cc per 1 liter.

Figure 6:
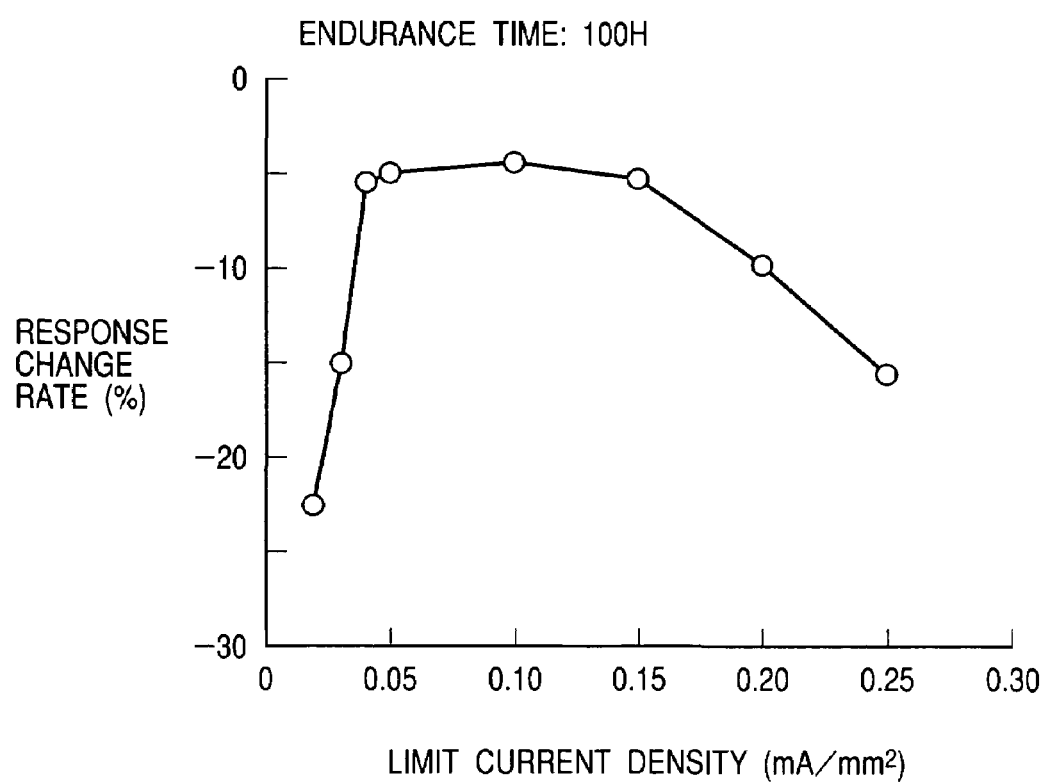
FIG. 6 is a graph showing a relationship between a limit current density and a response change rate in accordance with the preferred embodiment of the present invention.

Then, the response was evaluated in the above-described manner to obtain a change rate of the response compared with a reference value obtained before the endurance test was performed. FIG. 6 shows a relationship between a measured response change rate and a limit current density obtained through the endurance test.

According to FIG. 6, the response change rate is large in the region where the limit current density is less than 0.04 mA/mm² and also large in the region where the limit current density is larger than 0.15 mA/mm². On the other hand, a stable and excellent response characteristics is obtained in the region where the limit current density is in a range from 0.04 mA/mm² to 0.15 mA/mm².

In this manner, the gas sensing element 1 of this embodiment comprises the electrode protecting layer 17 satisfying the requirement that the limit current density of an oxygen ion current flowing between electrodes 15 and 16 is in the above-described range. Accordingly, it becomes possible to prevent the electrode protecting layer from being clogged or blocked by poisonous substances contained in the measured gas. It becomes possible to obtain a gas sensing element having excellent endurance. Furthermore, the measured gas can smoothly flow across the electrode protecting layer. Thus, even when the oxygen concentration in a measured gas changes rapidly, it becomes possible to obtain a sensor output varying quickly according to a change of the oxygen concentration.

As described above, the disclosed embodiment of the present invention provides a gas sensing element having excellent response and anti-poisoning endurance.

Furthermore, to check the properties of electrode protecting layer 17, a test piece was fabricated by sintering the above-described green sheet at 1,500° C. for one hour.

The thickness of this test piece was measured by a micrometer. An average pore diameter of the test piece was measured according to the mercury injection method. And, a gas permeation rate was measured according to the Blaine's permeation measuring method. The gas permeation rate was calculated based on the following Kozeny-Carman equation.

$$u = \{\epsilon^2/(1-\epsilon)^2\}\{\Delta P/\mu Sv^2 Lk\}$$

where u represents a permeation rate (cm/sec), $\epsilon$ represents a cavity rate of the tested sample, $\Delta P$ represents a pressure difference (g/cm²), $\mu$ represents an air viscosity coefficient (poise), Sv represents a surface to volume ratio evaluated on solid-volume base (cm²/cm³), L represents a sample thickness, and k represents a Kozeny constant=5.

As a result, it was confirmed that the electrode protecting layer 17 had a thickness of 160 μm, an average pore diameter of 2,600 Å, and a permeation rate of 0.3 cm/sec·atm.

Furthermore, various electrode protecting layers were prepared to perform the similar measurement. The prepared samples of the electrode protecting layer were differentiated in the thickness as well as in the average pore diameter (i.e., porosity) for the use of lamination layers and for the purpose of tests.

Regarding the samples of the electrode protecting layer for the test purpose, its properties were checked in the above-described manner.

FIG. 8 shows the measurement result, in which an ordinate represents the gas permeation rate and an abscissa represents the thickness. The lines in FIG. 8 are assortment of the measurement data according to the average pore diameter and the porosity. The porosity was evaluated according to the mercury injection method.

As understood from FIG. 8, the gas permeation rate decreases with increasing thickness and with decreasing average pore diameter.

On the other hand, each sample for the lamination use was incorporated into a gas sensing element so as to serve an electrode protecting layer according to the above-described manufacturing method. To satisfy the optimized range of 0.04 mA/mm² to 0.15 mA/mm², the gas permeation rate must be in a range from 0.03 cm/sec·atm to 1.5 cm/sec·atm. Regarding the thickness, the heat mass increases with increasing thickness. Having a large heat mass is not desirable to promptly warm up or activate the gas sensing element. On the contrary, reduction of the thickness will be restricted to a certain degree in consideration of easy handling of the sheet. Hence, it is desirable that the film thickness is in a range from 100 μm to 250 μm so as to satisfy the above-described gas permeation rate.

Even when the arrangement of the gas sensing element is modified, similar effects will be obtained as far as the electrode protecting layer satisfies the above-described requirements of this embodiment.

Figure 7:
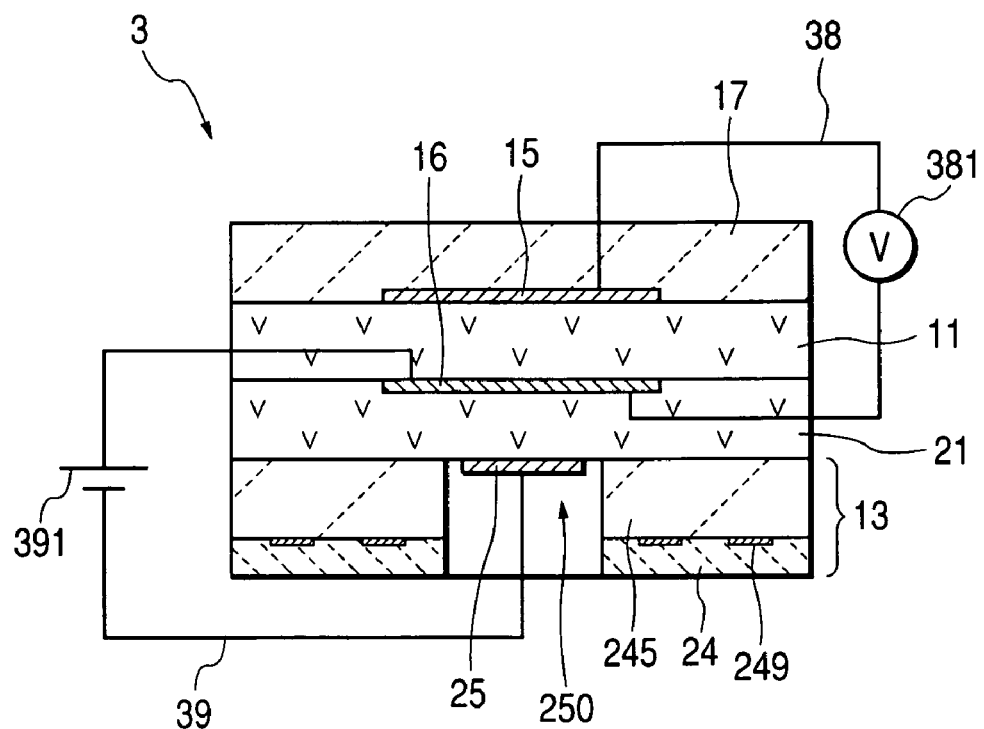
FIG. 7 is a cross-sectional view showing another gas sensing element in accordance with the preferred embodiment of the present invention.

FIG. 7 shows such a modified gas sensing element 3 which comprises a measured gas side electrode 15 provided on one surface of a solid electrolytic substrate 11 so as to be exposed to a measured gas, a reference gas side electrode 16 provided on the other surface of the solid electrolytic substrate 11. Like the above-described gas sensing element 1, the measured gas side electrode 15 is covered by a porous electrode protecting layer 17.

The reference gas side electrode 16 is covered by another solid electrolytic substrate 21. A heater 13, having a hollow space 250, is provided next to the solid electrolytic substrate 21. Another electrode 25 is provided on a surface of this solid electrolytic substrate 21 so as to be located in the hollow space 250.

A circuit 38 including a voltmeter 381 is connected between the electrodes 15 and 16. A circuit 39 including a power source 391 is connected between the electrodes 16 and 25. When a predetermined voltage is applied from the power source 391, oxygen molecules in the space 250 are ionized on the electrode 25 and conveyed to the vicinity of the electrode 16.

As the electrode 15 is exposed to the measured gas, the combination of the electrodes 15, 16 and the solid electrolytic substrate 12 functions as a cell producing an electromotive force representing an oxygen concentration. Thus, the oxygen concentration in the measured gas can be known by measuring the generated electromotive force by the voltmeter 381.

Although the type of the electrodes are different from those of the gas sensing element 1, the gas sensing element 3 brings the similar effects as the detecting principle of the present invention is applicable to the measurement of the electromotive force.

What is claimed is:

1. A gas sensing element comprising:
a solid electrolytic substrate having oxygen ion conductivity;
a measured gas side electrode provided on a surface of said solid electrolytic substrate so as to be exposed to a measured gas;
a reference gas side electrode provided on another surface of said solid electrolytic substrate so as to be exposed to a reference gas; and a single porous electrode protecting layer directly contacting and entirely covering said measured gas side electrode,
wherein a limit current density of said electrode protecting layer is in a range from 0.04 mA/mm² to 0.15 mA/mm² on a unit area of said reference gas side electrode under the following conditions:
an oxygen concentration in said measured gas is 0.1%, a measurement temperature and an element surface temperature at the measured gas side of a sensing portion are not less than 600° C., and a voltage applied between the measured gas side electrode and said reference gas side electrode is 0.5V.

2. The gas sensing element in accordance with claim 1, wherein said solid electrolytic substrate and said electrode protecting layer are integrated into a lamination body.

3. The gas sensing element in accordance with claim 1, wherein said solid electrolytic substrate and said electrode protecting layer are sintered together.

4. The gas sensing element in accordance with claim 1, wherein said solid electrolytic substrate and said electrode protecting layer are integrated into a lamination body and then sintered together.

5. The gas sensing element in accordance with claim 1, further comprising a heater.

6. The gas sensing element in accordance with claim 5, wherein said heater comprises an insulating substrate and a heater substrate having a heater element provided on a surface thereof.

7. The gas sensing element in accordance with claim 5, wherein a reference gas chamber is defined between said solid electrolytic substrate and said heater.

8. A gas sensing element in accordance with claim 7, further comprising a spacer disposed between said heater and said solid electrolytic substrate and defining a peripheral wall of said reference gas chamber.

9. The gas sensing element in accordance with claim 1, wherein a gas permeation rate of said detecting layer is 0.03 cm/sec·atm to 1.5 cm/sec·atm.

10. The gas sensing element in accordance with claim 1, wherein a thickness of said electrode protecting layer is in a range from 100 $\mu$m to 250 $\mu$m.

11. The gas sensing element in accordance with claim 1, wherein the electrode protecting layer has a thickness of 160 $\mu$m and an average pore diameter of 2,600 Å and a permeation rate of 0.03 cm/sec·atm.

* * * * *